Figure 1:
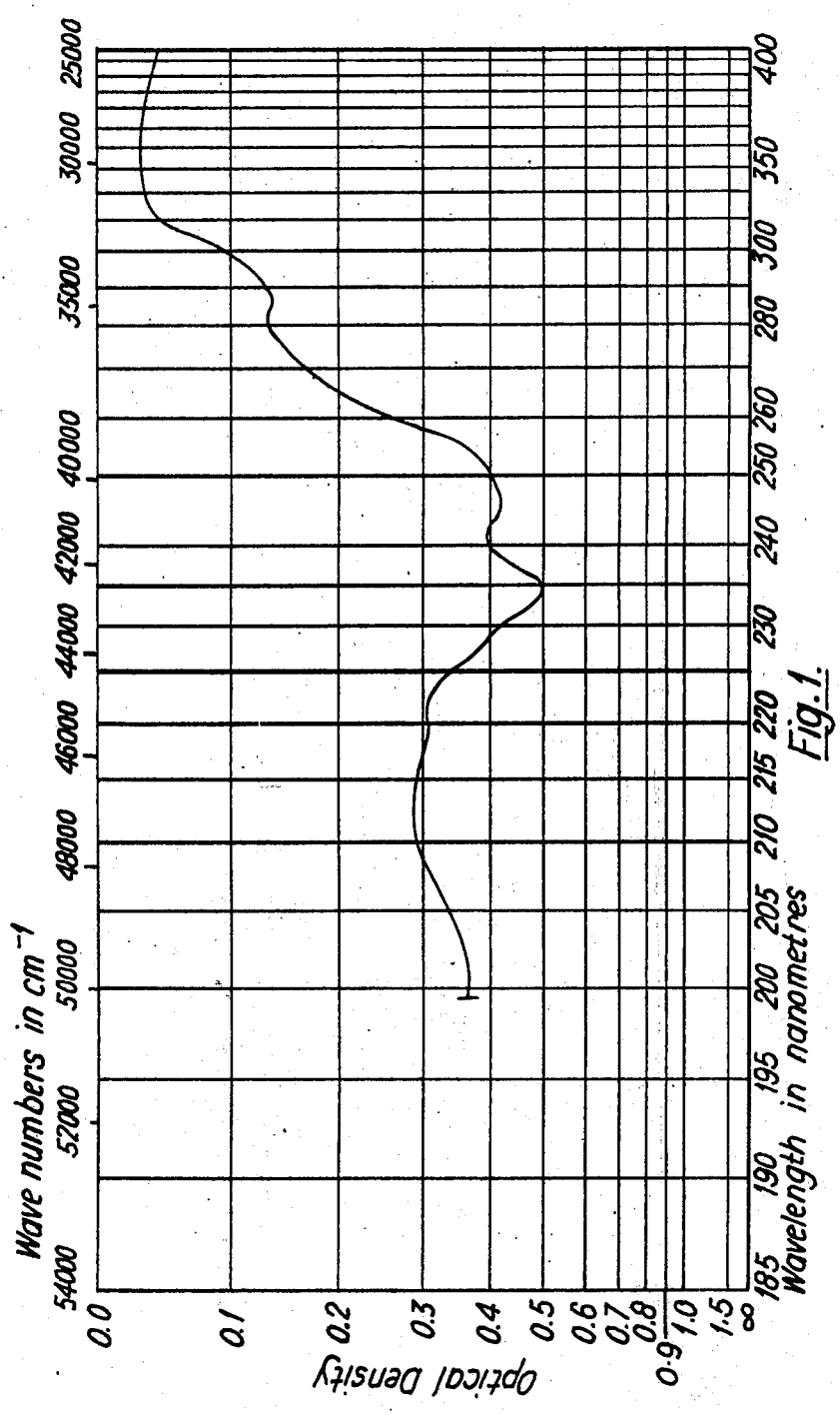

United States Patent [19]

Jolles et al.

[11] 3,970,641
[45] July 20, 1976

[54] ANTIBIOTIC 27,706 RP AND SALT THEREOF

[75] Inventors: Georges Jolles; Gérard Ponsinet, both of Sceaux, France

[73] Assignee: Rhone-Poulenc S.A., Paris, France

[22] Filed: Jan. 19, 1972

[21] Appl. No.: 219,065

[30] Foreign Application Priority Data
Jan. 20, 1971 France .............................. 71.01793
Nov. 23, 1971 France .............................. 71.41849

[52] U.S. Cl. ............................. 536/17; 195/80 R; 424/180
[51] Int. Cl.² ..................................... C07H 15/00
[58] Field of Search ....... 260/210 AB, 210 K, 210 R

[56] References Cited
UNITED STATES PATENTS

| | | | |
|---|---|---|---|
| 3,496,196 | 2/1970 | Suami et al. .................... | 260/210 R |
| 3,590,028 | 6/1971 | Arcamone et al. ............ | 260/210 AB |
| 3,686,163 | 8/1972 | Arcamone et al. ............ | 260/210 AB |

*Primary Examiner*—Johnnie R. Brown
*Attorney, Agent, or Firm*—Stevens, Davis, Miller & Mosher

[57] ABSTRACT

Antibiotics 20,798 RP and 27,706 RP of the general formula:

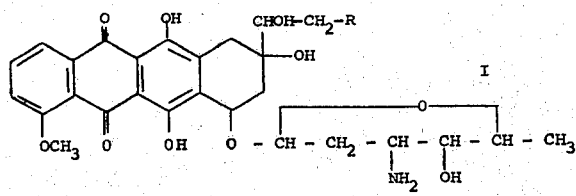

(wherein R represents a hydrogen atom or a hydroxy group) or acid addition salts thereof are prepared by reduction of a corresponding compound wherein the —CHOH—CH₂—R group is replaced by

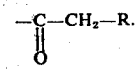

The antibiotics of general formula I have valuable anti-tumour properties; that wherein R is hydroxy (27,706 RP) is new.

2 Claims, 3 Drawing Figures

ANTIBIOTIC 27.706 RP AND SALT THEREOF

The present invention relates to a process for the preparation of antibiotics possessing valuable anti-tumour properties and to a new antibiotic.

According to the present invention, there is provided a process for the preparation of an antibiotic of the general formula:

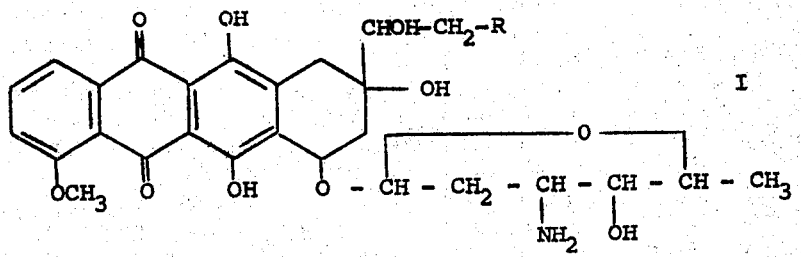

(wherein R represents a hydrogen atom or a hydroxy group) or an acid addition salt thereof which comprises reducing a compound of the general formula:

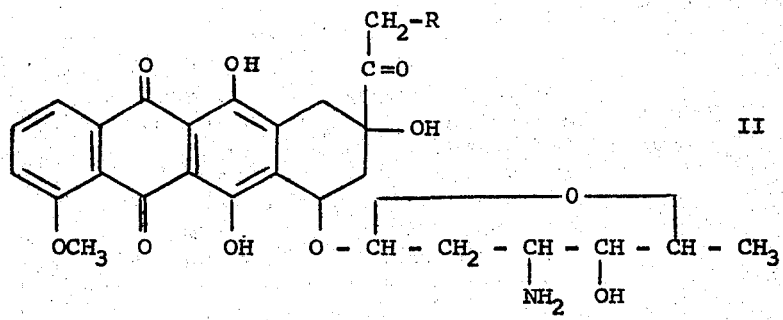

(wherein R is as hereinbefore defined) or an acid addition salt thereof to convert the grouping —CO—CH$_2$—R to —CHOH—CH$_2$—R.

The reduction of the compound of general formula II or an acid addition salt thereof, e.g. the hydrochloride, may be effected by means of an alkali metal borohydride, such as potassium borohydride, at a temperature of −20° to +30°C. The reaction is generally carried out in an alcohol, for example methanol or ethanol, as solvent or in a mixture of solvents such as a mixture of methanol and chloroform or of ethanol and chloroform.

The compounds of general formula I, which may be isolated as the free bases or in the form of their acid addition salts, such as the hydrochloride, can be purified by physico-chemical methods such as crystallisation or chromatography. The free bases prepared by the aforementioned process may, where appropriate, be converted into acid addition salts. The salts may be obtained by the reaction of the bases of formula I with acids in appropriate solvents. As organic solvents there may be used, for example, alcohols, ethers, ketones or chlorinated hydrocarbons. The salt which is formed is precipitated, if necessary after concentration of its solution, and is separated by filtration or decantation.

The starting material of general formula II wherein R represents a hydrogen atom is the antibiotic designated by the number 13,057 RP which has been given the name "daunorubicin". Daunorubicin may be obtained by isolation, using countercurrent distribution methods, from the antibiotic designated 9865 RP of which it is a constituent. 9865 RP may be produced by cultivating aerobically Streptomyces 8899 or Streptomyces 31723 or a 9865 RP productive mutant thereof in a nutrient medium containing assimilable sources of carbon, nitrogen, and mineral salts until substantial antibiotic activity is produced by the said microorganism in the said medium and recovering the antibiotic 9865 RP from the medium. The microorganisms Streptomyces 8899 and Streptomyces 31723, the antibiotics 9865 RP and daunorubicin, and the preparation of daunorubicin and its acid addition salts by preparation of 9865 RP using Streptomyces 8899 and 31723 and isolation from the product are described in British Patent Specification No. 985,598. Streptomyces 8899 and Streptomyces 31723 have been deposited at the Northern Regional Research Laboratory, United States of America under the numbers NRRL 3046 and NRRL 3045 respectively. Samples of the microorganisms may be obtained from the Northern Regional Research Laboratory on request.

The starting material of general formula II wherein R represents a hydroxy group is the antibiotic which has been given the name "adriamycin". Adriamycin may be prepared by cultivation of Streptomyces peucetius var, caesius (F.I. 106 of the Farmitalia microbiological collection) under aerobic conditions in a liquid nutrient medium containing an assimilable source of carbon, an assimilable source of nitrogen and mineral salts. The microorganism Streptomyces peucetius var. caesius F.I. 106, the antibiotic adriamycin and the preparation of adriamycin and its acid addition salts using Streptomyces peucetius var, caesius are described in British Patent Specification No. 1,161,278. Streptomyces peucetius var. caesius has been deposited at the Commonwealth Mycological Institute, Ferry Lane, Kew, Surrey, England, where it received the index number I.M.I. 131.502 and at the Institute of Microbiology at Rutgers University, United States of America where it received the index number I.M.R.U. 3920. Samples of the microorganism are available from the Commonwealth Mycological Institute on request.

The antibiotic of general formula I wherein R represents a hydrogen atom is designated by the number 20,798 RP and has been given the name "duborimycin". This antibiotic, its manner of use in anti-tumour treatment, particularly in the treatment of lymphoblastic and myeloblastic leukaemias, and its preparation by cultivation of Streptomyces coeruleorubidus (deposited at the Northern Regional Research Laboratory, U.S.A. under the number NRRL 3045) and separation of 20,798 RP formed during the culture have been described in British Patent Specification No. 1,226,494, and its French equivalent, French Patent Specification No. 1,583,752.

Thin layer chromatography and infra-red and nuclear magnetic resonance spectroscopy establish that the antibiotic of general formula I wherein R represents a hydrogen atom, obtained by the process according to the invention, and the antibiotic 20,798 RP obtained by cultivation of Streptomyces coeruleorubidus (NRRL 3045) as described in British Patent No. 1,226,494 and French Patent No. 1,583,752 are identical.

The antibiotic of general formula I wherein R represents a hydroxy group is new and forms part of the present invention. The antibiotic, hereinafter designated 27,706 RP, can exist in the form of the free base or an acid addition salt thereof such as the hydrochloride.

The free base of the antibiotic 27,706 RP has the following characteristics:

Appearance: red powder
Melting point: 238°–244°C
Ultra-violet spectrum: (determined in a 10 mg/l solution in ethanol)
Absorption maximum at 286 nm, $\epsilon = 7,200$
Absorption maximum at 247 nm, $\epsilon = 22,640$
Absorption maximum at 234.5 nm, $\epsilon = 27,000$
Shoulder at about 257 nm.

This spectrum is shown in FIG. 1 of the accompanying drawings in which the abscissae give the wavelength expressed in nanometers (lower scale) and the wave number in $cm^{-1}$ (upper scale), and the ordinate gives the optical density.

Figure 2:
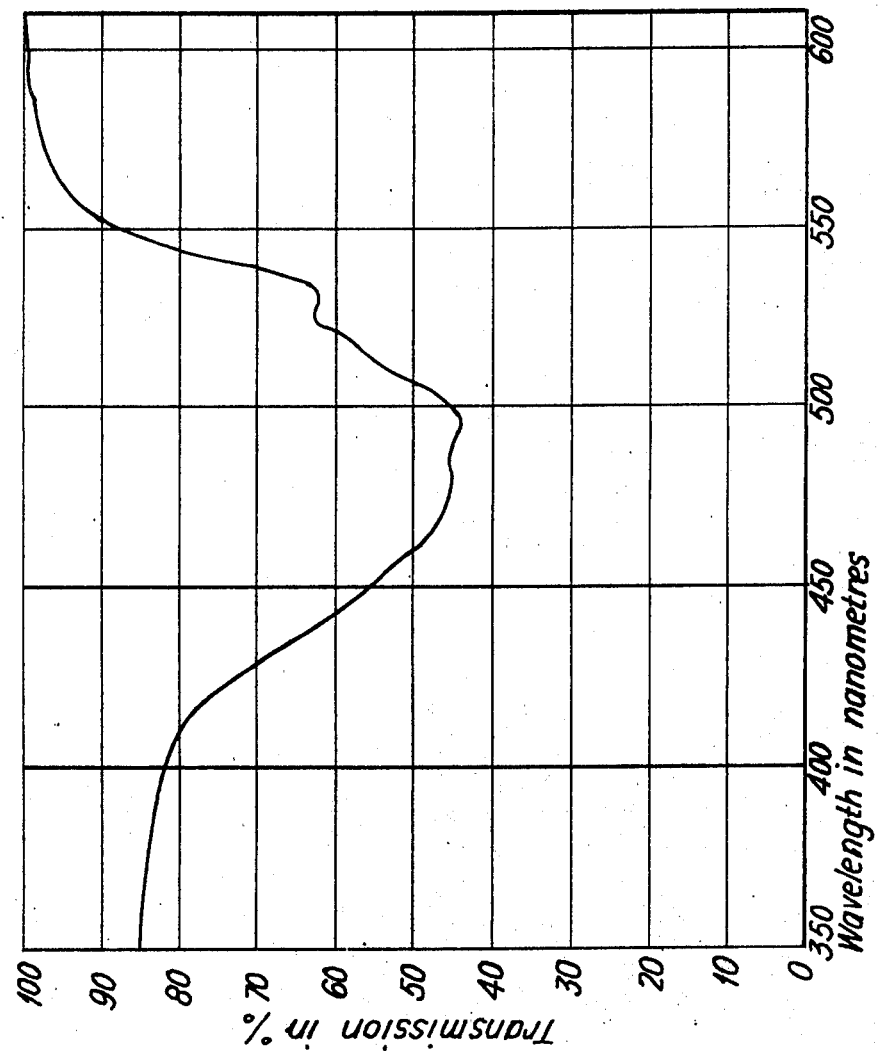

Visible spectrum: (determined using a 20 mg/l solution in ethanol)
Absorption maximum at 531 nm, $\epsilon = 5,675$
Absorption maximum at 495 nm, $\epsilon = 9,740$
Absorption maximum at 481 nm, $\epsilon = 9,465$ This spectrum is shown in FIG. 2 of the accompanying drawings in which the abscissa gives the wavelength expressed in nanometers and the ordinate gives the transmission expressed as a percentage.

Infra-red spectrum: (determined using tablets of a mixture with KBr)

Figure 3:
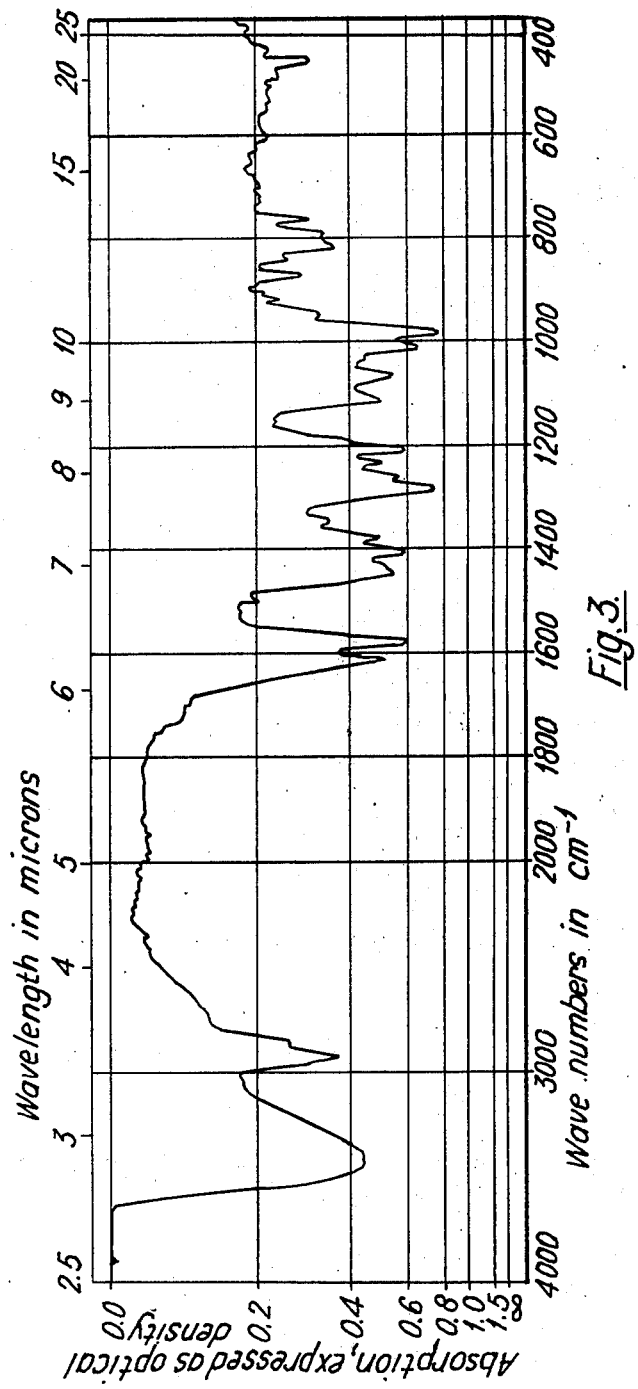

This spectrum is shown in FIG. 3 of the accompanying drawings wherein the abscissae give the wavelength expressed in microns (upper scale) and the wave number in $cm^{-1}$ (lower scale) and the ordinate gives the absorption as optical density.

The principal infra-red absorption bands (in $cm^{-1}$) of antibiotic 27,706 RP are shown in Table I below.

TABLE I

| | | | |
|---|---|---|---|
| 3,395 m | 1,445 s | 1,030 sh | 705 w |
| 3,280 sh | 1,408 s | 1,010 s | 690 w |
| 3,040 sh | 1,378 m | 982 vs | 685 sh |
| 2,960 sh | 1,345 m | 950 m | 667 w |
| 2,930 s | 1,283 vs | 915 m | 650 vw |
| 2,860 m | 1,262 m | 885 sh | 600 m |
| 2,720 sh | 1,234 m | 880 sh | 550 w |
| 1,720 sh | 1,209 s | 870 m | 528 w |
| 1,655 sh | 1,190 vw | 840 w | 500 vw |
| 1,612 s | 1,187 sh | 11 815 m | 480 sh |
| 1,575 vs | 1,150 sh | 795 w | 460 m |
| 1,557 vw | 1,113 s | 760 m | 433 w |
| 1,498 w | 1,080 sh | 730 m | 415 sh |
| 1,470 sh | 1,067 s | 720 vw | 393 w |

TABLE I-continued vs = very strong
s = strong
m = medium
w = weak
vw = very weak
sh = shoulder The antibiotic 27,706 RP has substantially the same anti-tumour activity properties as duborimycin. It has proved particularly active against graftable tumours in mice such as the solid form of sarcoma 180 and leukaemia L 1,210.

For therapeutic purposes, the antibiotic 27,706 RP may be employed as such or in the form of non-toxic acid addition salts, i.e. salts containing anions which are relatively innocuous to the animal organism in therapeutic doses of the salts, such as hydrochlorides, sulphates, nitrates, phosphates, acetates, propionates, succinates, benzoates, fumarates, maleates, tartrates, theophylline-acetates, salicylates, phenolphthalinates or methylene-bis-$\beta$-hydroxynaphthoates.

The following Examples illustrate the present invention.

EXAMPLE 1

Potassium borohydride (228 mg.) is added in small portions to a stirred solution of daunorubicin hydrochloride (1.2 g.) in a chloroform-ethanol mixture (5—5 by volume; 100 cc.), at 20°C. The reaction mixture is stirred for a further 4 hours at 20°C. The mixture is filtered and the precipitate is washed with a chloroform-ethanol mixture (5—5 by volume; 20 cc.).

The filtrate and the wash liquors are combined and concentrated to dryness under reduced pressure (17 mm.Hg) at 30°C. The solid residue is dissolved in a chloroform-n-butanol mixture (8-2 by volume; 100 cc.). An 0.1N sodium hydroxide solution is added, with stirring to this solution until the pH of the aqueous phase reaches 8.6. After washing with water and then decanting, the organic phase is adjusted to pH 3.5 by addition of 0.1N hydrochloric acid. The mixture is concentrated under reduced pressure (17 mm.Hg) at 50°C to a volume of 20 cc. A precipitate appears. Acetone (100 cc.) is added to complete the precipitation. The mixture is filtered and the precipitate is washed with a n-butanol-acetone mixture (1—5 by volume; 20 cc.) and dried under reduced pressure (0.3 mm. Hg) at 20°C.

After recrystallisation from a methanol-dioxan mixture, duborimycin hydrochloride (1 g.; m.p. 222-228°C) is obtained.

Elementary analysis: C = 57.3% (theory : 57.29%), H = 5.9% (theory : 5.69%), N = 2.7% (theory : 2.47%), Cl = 6.2% (theory : 6.26%).

EXAMPLE 2

Potassium borohydride (393 mg.) is added in small portions, over the course of 30 minutes, to a stirred solution of daunorubicin hydrochloride (15 g.) in methanol (150 cc.) at −15°C. Stirring is continued for 30 minutes at −15°C. A mixture (600 cc.), previously cooled to 0°C, of chloroform-n-butanol (8-2 by volume) is added, followed by a solution of N ammonium hydroxide (26.6 cc.) in methanol (50 cc.) at 0°C. Water (200 cc.) is added, the mixture is separated by decantation and the organic phase is then washed with iced water (2 × 200 cc.). The organic solution is dried over sodium sulphate and concentrated to dryness under a reduced pressure of 1 mm.Hg at 30°C and then 0.1 mm.Hg at 20°C. The residue is taken up in a chloroform-n-butanol mixture (8-2 by volume; 60 cc.). A solution of N hydrochloric acid (25.5 cc.) in methanol (20 cc.) is added. Diethyl ether (400 cc.) is added and the precipitate formed is filtered off and washed with diethyl ether.

The red solid obtained is recrystallised by dissolving it in methanol (25 cc.) and adding dioxan (70 cc.). After cooling, filtration yields duborimycin hydrochloride (12.35 g.) melting at 222°–228°C.

Elementary analysis:
C = 56.7% (theory : 57.29%), H = 6.1% (theory : 5.69%), N = 2.3 % (theory : 2.47%), Cl = 5.6% theory : 6.26%).

EXAMPLE 3

Potassium borohydride (10 mg.) is added, at −15°C, to a stirred solution of adriamycin (79 mg.), in the form of the base, in a mixture of methanol (5 cc.) and chloroform (2 cc.). Stirring is continued for 50 minutes at −15°C. A mixture (10 cc.), previously cooled to 0°C, of chloroform-n-butanol (8-2 by volume) is added, followed by distilled water (5 cc.) at 0°C. The organic phase is decanted off and the aqueous phase is again extracted with a chloroform-n-butanol mixture (8-2 by volume; 10 cc.). The organic phases are combined and washed with iced water (3 × 5 cc.). The organic solution is dried over sodium sulphate and is concentrated to dryness under a reduced pressure of 1 mm.Hg at 30°C and then at 0.1 mm.Hg at 20°C.

The residue is taken up in methanol (10 cc.). The mixture is filtered, the insoluble matter is washed with methanol and the filtrate is concentrated to dryness under reduced pressure (1mm.Hg) at 30°C.

Antibiotic 27,706 RP (23 mg.), m.p. 238°–244°C, is obtained.

Elementary analysis: N = 2.25% (theory : 2.57%).

The present invention includes within its scope pharmaceutical compositions comprising the antibiotic 27,706 R.P. in association with a compatible pharmacologically acceptable carrier and/or a compound which may itself be physiologically active, for example an antibiotic. These compounds may be made up in any pharmaceutical form appropriate for the route of administration in question.

Solid compositions for oral administration include compressed tablets, pills, dispersible powders, and granules. In such solid compositions, the new antibiotic is admixed with at least one inert diluent such as calcium carbonate, potato starch, alginic acid, or lactose.

The compositions may also comprise, as is normal practice, additional substances other than inert diluents, e.g. lubricating agents, such as magnesium stearate. Liquid compositions for oral administration include pharmaceutically acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules, of absorbable material such as gelatin containing the antibiotic with or without the addition of diluents or excipients.

Preparations according to the invention for parenteral administration include sterile aqueous or non-aqueous solutions, suspensions, or emulsions. Examples of non-aqueous solvents or suspending media are propylene glycol, vegetable oils such as olive oil, and injectable organic esters such as ethyl oleate. These compositions may also contain adjuvants such as preserving, wetting, emulsifying and dispersing agents. They may be sterilised by, for example, filtration through bacteria-retaining filter, by incorporation in the compositions of sterilising agents, by irradiation, or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. Generally solutions suitable for parenteral administration contain 0.001 to 1% by weight of the antibiotic.

The following Example illustrates a pharmaceutical composition according to the invention.

EXAMPLE 4

Tablets containing 1 mg. of active product and having the following composition are prepared by a conventional method.

| | |
|---|---|
| antibiotic 27,706 RP | 0.001 g |
| starch | 0.081 g |
| precipitated silica | 0.016 g |
| magnesium stearate | 0.002 g |

We claim:
1. The antibiotic herein designated 27,706 RP of the formula:

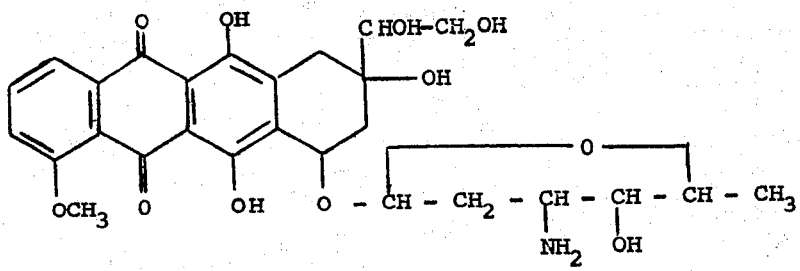

and non-toxic acid addition salts thereof.
2. The hydrochloride of the antibiotic 27,706 RP as defined in claim 1.

* * * * *